US008999892B2

(12) United States Patent  
Quaghebeur

(10) Patent No.: US 8,999,892 B2
(45) Date of Patent: Apr. 7, 2015

(54) USE OF S-ABSCISIC ACID FOR IMPROVING FRUIT SET AND PRODUCING PARTHENOCARPIC FRUITS AND AS A GROWTH INHIBITOR

(75) Inventor: Koen Quaghebeur, Sint-Truiden (BE)

(73) Assignee: Globachem, Sint-Truiden (BE)

( * ) Notice: Subject to any disclaimer, the term of this patent is extended or adjusted under 35 U.S.C. 154(b) by 2012 days.

(21) Appl. No.: 11/573,832

(22) PCT Filed: Aug. 16, 2005

(86) PCT No.: PCT/EP2005/008850
§ 371 (c)(1),
(2), (4) Date: May 21, 2007

(87) PCT Pub. No.: WO2006/018266
PCT Pub. Date: Feb. 23, 2006

(65) Prior Publication Data
US 2008/0318787 A1    Dec. 25, 2008

(30) Foreign Application Priority Data

Aug. 17, 2004 (DE) .......................... 10 2004 039 736

(51) Int. Cl.
*A01N 37/40* (2006.01)
*A01N 49/00* (2006.01)
(52) U.S. Cl.
CPC ................ *A01N 49/00* (2013.01); *A01N 37/40* (2013.01)
(58) Field of Classification Search
CPC ................................. A01H 3/04; A01N 37/40
USPC ......................................................... 504/320
See application file for complete search history.

(56) References Cited

U.S. PATENT DOCUMENTS 5,173,106 A    12/1992  Kamuro et al.
2005/0198896 A1  9/2005  Quaghebeur

FOREIGN PATENT DOCUMENTS

JP    6100406 A     4/1994
WO    03/096806 A2  11/2003

OTHER PUBLICATIONS

Kim Bong Ho et al., Effects of natural ABA and AVG on the inhibition of berry shattering in 'Kyoho' grapes, Journal of Korean Society for Horticultural Science, 39(4): 433-436 (1998); English language abstract, BIOSIS Online! Biosciences Information Service, Database accession No. PREV199800480172, Aug. 1998.
Koshita Yoshiko et al., Involvement of endogenous plant hormones (IAA, ABA, GAs) in leaves and flower bud language abstract, BIOSIS Online! Biosciences Information Service, Database accession No. PREV199900085149, Feb. 1999.
Duan Cheng-Guo et al., Effects of removing scales and exogenous hormone treatments on changes of endogenous hormone in sweet cherry flower buds and dormancy release during dormancy, Xibei Zhiwu Xuebao, 24(4): 616-620 (2004); English language abstract, BIOSIS Online! Biosciences Information Service, Database accession No. PREV200400346398, Apr. 2004.
Garcia-Luis A et al., Inhibition of flowering in-vivo by existing fruits and applied growth regulators in Citrus Unshiu, Physiologia Plantarum, 66(3): 515-520 (1986); English language abstract, BIOSIS Online! Biosciences Information Service, Database accession No. PREV198682017466, 1986.
Shukla Amit et al., Abscisic acid: One of the factors affecting male sterility in *Brassica napus*, Physiologia Plantarum, 91(3): 522-528 (1994); English language abstract, BIOSIS Online! Biosciences Information Service, Database accession No. PREV199497424322, 1994.
Tamura Fumio et al., Relationship between intensity of bud dormancy and level of ABA in Japanese pear Nijisseiki, Journal of Japanese Society for Horticultural Science, 62(1): 75-81 (1993); English language abstract, BIOSIS Online! Biosciences Information Service, Database accession No. PREV199396051664, 1993.
Vanderhoven, CH. et al., Analysis of orthonil in different biological tests for growth. Comparison with phytohormones, Mededelingen van de Faculteit Landbouwwetenschappen Universiteit Gent, 37(2): 623-633 (1972); English language abstract, CA Online! Chemical Abstracts Service, Database accession No. 1973:449722, 1973.
Konings, Henk et al., Promotion and inhibition by plant growth regulators of aerenchyma formation in seedling roots of *Zea mays*, Physiologia Plantarum, 60(3): 309-314 (1984) ; English language abstract, CA Online! Chemical Abstracts Service, Database accession No. 1984:418951, 1973.
Xu, Hui Lian et al., Effects of epibrassinolide and abscisic acid on sorghum plants growing under soil water deficit. I. Effects on growth and survival, Nippon Sakumotsu Gakkai Kiji, 63(4): 671-675 (1994); English language abstract, CA Online! Chemical Abstracts Service, Database accession No. 1995:269107, 1995.
Matsui Shuchiro et al., Growth analysis of onion (*Allium cepa* L.) plants treated with (S)-(+)-ascisic acid, Gifu Daigaku Nogakubu Kenkyu Hokoku, 59: 57-62 (1994); English language abstract, CA Online ! Chemical Abstracts Service, Databae accession No. 1995:505942, 1995.
Byun, Jae-Kyun et al., Effects of GA3, thidiazuron and ABA on fruit set and quality of 'Kyoho' grapes , Han'guk Wonye Hakhoechi, 36(2): 231-239 (1995); English language abstract, CA Online! Chemical Abstracts Service, Database accession No. 1995:633507, 1995.
Xing, Xin Hui et al., Effect of abscisic acid on shoot regeneration from rice (*Oryza sativa* L.) callus, Nippon Shokubutsu Soshiki Baiyo Gakkai, 12(2): 125-130 (1995); English language abstract, CA Online! Chemical Abstracts Service, Database accession No. 1995:784757, 1995.
Shen, Jiaxiang et al., Comparison of the biological activity of natural (S)-(+)-ABA and non-natural (R)-(−)-ABA, Zhiwu Shengli Xuebao, 21(2): 166-174 (1995); English language abstract, CA Online! Chemical Abstracts Service, Database accession No. 1995:793486, 1995.

(Continued)

*Primary Examiner* — Rebecca Prouty
*Assistant Examiner* — Danielle Sullivan
(74) *Attorney, Agent, or Firm* — Panitch Schwarze Belisario & Nadel LLP

(57) ABSTRACT

S-abscisic acid is used for promoting fruit set and/or for producing parthenocarpic fruits in useful plants. S-abscisic acid is also used as a growth inhibitor in useful plants. Methods are provided for treating useful plants with S-abscisic acid for these purposes.

10 Claims, No Drawings

(56) References Cited

OTHER PUBLICATIONS

Kamal, Muhammad et al., Analysis of soybean yield components as affected by plant growth regulators applied at flowering stages, Nippon Nettai Nogyo Gakkai, 39(3): 184-189 (1995); English language abstract, CA Online! Chemical Abstracts Service, Database accession No. 1995:964469, 1995.

Kim, Bong Ho et al., Effects of natural type ABA and AVG the inhibition of berry shattering in "Kyoho" grapes, Han'guk Wonye Hakhoechi, 39(4): 433-436 (1998); English language abstract, CA Online! Chemical Abstracts Service, Database accession No. 1998:625675, 1998.

Saniewski, Marian et al., Inhibitory effect of abscisic acid on shoot growth and flowering induced by gibberellic acid in nonprecooled derooted bulbs of tulip (*Tulipa gesneriana* L.), Journal of the Faculty of Agriculture, Kyushu University, 44(1-2): 25-32 (1999); English language abstract, CA Online! Chemical Abstracts Service, Database accession No. 2000:14511, 2000.

Onjo, Michio et al., Effects of plant growth regulators on plantet growth and enlargement of microtubers of water yam (*Discorea Alata* L.) in vitro, Nippon Nettai Nogyo Gakkai Jimukyoku, 45(2): 142-147 (2001); English language abstract, CA Online! Chemical Abstracts Service, Database accession No. 2001:596995, 2001.

Zhang, Shaoling et al., Effects of plant growth regulating substances on pollen germination and tube growth in Fengshui pear (*Pyrus serotina*), Xibei Zhiwu Xuebao, 23(4): 586-591 (2003); English language abstract, CA Online! Chemical Abstracts Service, Database accession No. 2004:618030, 2004.

USE OF S-ABSCISIC ACID FOR IMPROVING FRUIT SET AND PRODUCING PARTHENOCARPIC FRUITS AND AS A GROWTH INHIBITOR

CROSS-REFERENCE TO RELATED APPLICATIONS

This application is a Section 371 of International Application No. PCT/EP2005/008850, filed on Aug. 16, 2005 in the European Patent Office, which was published in the German language on Feb. 23, 2006, under International Publication No. WO 2006/018266 A1 and the disclosure of which is incorporated herein by reference.

BACKGROUND OF THE INVENTION

For reasons of profitability, the cultivation of useful plants in agriculture or in horticulture aims at achieving high crop yields and at achieving this with as little input of material, such as fertilizers and pesticides, and as little expenditure of labor as possible. Where environmentally friendly cultural methods are employed in order to produce so-called bioproducts, an additional factor is that the use of chemical fertilizers or plant protectants has to be largely or entirely dispensed with.

An increase in yield may generally be achieved by increasing the volume of the harvest crop. This, in turn, can be achieved by promoting flower formation, by promoting fruit set and by increasing the size and weight of the individual pieces of fruit.

After flowering or after fruit setting, flower drop or premature fruit drop occur frequently due to atmospheric influence; this further reduces the number of fruits. Hence, an increase in crop yield can also be affected by inhibiting flower drop or fruit set.

The term "fruit set" is generally understood to mean the percentage of flowers which have begun to develop into a fruit. Generally, the fruit set is 10 to 30%, depending on the year, the species, the variety, the flower density and the weather conditions.

Particularly in fruit trees it is frequently observed that a very heavy flowering is followed by an insufficient fruit set. The physiological processes underlying this phenomenon are still largely unclear. Fruit set is determined on the one hand by the physiological condition of the plant or fruit free, on the other hand it is also determined by the weather conditions during flowering, which are of crucial importance for pollen transmission (pollination) and for the viability and further development of the seed buds.

Measures adopted to promote fruit set are chemical or mechanical thinning methods (cutting measures) to thin the flowers, or dressing of leaves with nitrogen-containing fertilizers.

The above-mentioned thinning methods are disadvantageous as they cause additional expenditure of labor and additional costs; in addition, although the thinning promotes the fruit set in the remaining flowers, this is at the cost of the flowers removed by the thinning. The above-mentioned foliage dressing likewise involves additional expenditure of labor and additional costs; in addition, this measure cannot be used in ecological methods of cultivation.

A further problem in the cultivation of useful plants for producing fruits, particularly in orcharding, consists in that the plants exhibit increased vegetative growth, that is, an increased shoot growth with increased growth of herbage. In fruit trees, this growth usually starts with flowering and lasts up to approximately the middle of July; it ends with the closing of the buds.

This increased vegetative growth can lead to a reduction of the crop yield, as well as—owing to the formation of excessive shade—to detrimental effects on the fruit quality. Excessive shoot growth or longitudinal growth of the plants, especially of fruit trees, is also undesirable because it renders harvesting more difficult. Furthermore, excessive longitudinal growth can lead to the plants being damaged by wind, rain or hail since they are not able to withstand the mechanical stress. This particularly applies to rape and grain.

For this reason, repeated cutting measures or treatments with synthetic growth inhibitors are required in order to counteract this excessive growth. These cutting measures are very labor- and cost-intensive measures.

By using synthetic growth inhibitors, the extent of the cutting measures can be reduced. Several growth inhibitors suitable for this purpose are known, e.g. chlormequat, mepiquat chloride, triazole compounds, such as paclobutrazol, or acylcyclohexane diones, such as trinexapacethyl. It is disadvantageous, however, that these growth inhibitors have to be applied in high dosages per hectare and that they present a potential risk to the environment. For ecological or near-natural production of fruits, the use of such growth inhibitors is completely out of the question. This is also true of more recent types of growth inhibitors, which are active at lower dosages. Abscisic acid (ABA) is a phytohormone which in perennial ligneous plants is responsible for the initiation and maintenance of bud dormancy during the dormant period in winter. ABA is furthermore said to have an influence on the water balance of the plant, and it can inhibit seed germination. ABA is generally regarded as the stress hormone of plants, that is, ABA is produced above all under stress conditions (e.g. drought, or temperature-induced stress). As early as 1963 it was reported that endogenously produced ABA is responsible for leaf abscission in cotton. Under conditions of drought, ABA affects the closure of the stomata, which prevents further loss of water and thereby prevents that the plant dries up.

International Publication No. WO 03 096806 A2 mentions that ABA can cause defoliation (leaf abscission), fruit drop and dormancy, and that, in fruit trees, it is said to prevent resprouting caused by certain weather conditions. There are no details given as to the mode of application; in particular, the time of application and the dosage are not indicated.

International Publication No. WO 03 096806 A2 furthermore describes the use of ABA to prevent the cracking of cherries, to increase frost hardiness and to increase the sugar content in fruit.

U.S. Pat. No. 5,173,106 describes the use of ABA to inhibit flowering and to extend the duration of flowering in flowering plants.

BRIEF SUMMARY OF THE INVENTION

The invention relates to the use of S-abscisic acid to promote fruit set and to produce parthenocarpic fruits in useful plants, especially in fruit cultivation. The invention further relates to the use of S-abscisic acid as a growth inhibitor in useful plants, especially in fruit cultivation.

The invention furthermore encompasses methods for promoting fruit set, for producing parthenocarpic fruits, and for growth regulation in useful plants, especially in fruit crops.

The object of the present invention is therefore to overcome or avoid the above-described disadvantages and to indicate measures by which the fruit set in useful plants, especially in fruit trees, can be improved and by which unwanted vegetative growth in useful plants, especially fruit trees, can be reduced or suppressed. A further demand is that these measures be highly environmentally compatible and suitable for application in ecological farming or for the production of "biological" fruit.

In accordance with the invention, these objects are achieved by the use of S-abscisic acid (S-ABA) in useful plants to promote fruit set and/or to produce parthenocarpic fruits, as well as by the use of S-abscisic acid as a growth inhibitor in useful plants.

The objects are furthermore achieved by methods which are based on the application of S-ABA.

DETAILED DESCRIPTION OF THE INVENTION

It was shown, surprisingly, that S-ABA can be used to promote fruit set in useful plants. This effect is surprising first of all because ABA has been described as a plant hormone that is responsible for the initiation and maintenance of dormancy or for the inhibition of flowering and the prolongation of the duration of flowering, or for the induction of fruit drop.

Because of the ABA-induced improvement in fruit set, it is possible to increase the crop yield and to reduce the expenditure for conventional measures, such as cutting measures or leaf dressing, or to do without such measures altogether. The increase in yield is due to an increase in the average number of fruits that can be harvested from each plant, as well as to an increase in the total mass of fruits; it is not merely due to an increase in volume or weight of the individual pieces of fruit.

Since S-ABA is a naturally occurring phytohormone, its application is toxicologically harmless and it is also suitable for the purposes of biological agriculture.

Another surprising advantage of the present invention is that the application of S-ABA enables the production of parthenocarpic fruits.

The advantage thereof is that fruit setting takes place independently of pollination, so that even under unfavorable weather conditions—when pollination, for example by bees or other insects, is impossible or only possible to an insufficient extent—a sufficient fruit set will be achieved. The formation of parthenocarpic fruits is advantageous also if no sufficient pollination can take place for other reasons. Parthenocarpy in pome fruit has so far been described in literature only in certain pear varieties, where this phenomenon occurs spontaneously.

S-ABA-induced formation of parthenocarpic fruits has been observed particularly in pome fruit (e.g. apples, pears), and in these crops, in particular, it can be used to advantage.

A further advantage connected with the formation of parthenocarpic fruits consists in that these fruits (e.g. pipless apples or pears) do not promote alternation. Because there are no pips, these fruits are not responsible for the occurrence of alternation. This means that by treating plants with S-ABA an improved crop yield (with parthenocarpic fruits) is achieved, but, contrary to the alternation phenomenon, in the following year, too, a crop yield is achieved which is, at least, normal. Generally, the term "alternation" is used when a year with a heavy fruit load is followed by a year with a low fruit set and correspondingly lower crop yield. This behavior is known predominantly from pome fruit. It is genetically induced and can also be triggered by unfavorable environmental conditions (late frost, nutrient deficiency, infestation with disease or pests).

Surprisingly, it has further been shown that S-ABA can be used as a growth inhibitor for useful plants. S-ABA-induced growth inhibition is reflected substantially in an inhibition of the growth of the shoot axis and of the lateral shoots. The longitudinal growth of the shoots is suppressed, which leads to the shoots, which have been formed during the growth phase, on average exhibiting a smaller length as compared to plants not treated with S-ABA. This growth inhibition is recognizable by the fact that the closing of the buds occurs at a distinctly earlier point in time than in plants which have not been treated with S-ABA.

By using S-ABA as a growth inhibitor, it becomes possible to dispense with the, otherwise frequently applied, cutting measures or to reduce the extent of such measures. It thereby also becomes possible to dispense with the use of synthetic growth inhibitors or to reduce the dosage of such synthetic growth inhibitors. The fact that S-ABA has a growth-inhibiting effect comparable to that of synthetical growth inhibitors was not to be expected on the basis of the properties of S-ABA described in the technical literature.

S-ABA-induced growth inhibition furthermore leads to a higher quality of the fruits, for example an improved color, because of improved access of light and improved aeration. In addition, the risk and extent of infestation with pests and diseases is reduced, so that the use of pesticides can be reduced correspondingly. S-ABA-induced growth inhibition furthermore leads to the useful plants, especially fruit trees, producing a larger number of flowers and fruits in the subsequent year than would be the case without such treatment.

The use of S-ABA is in any case advantageous over the use of synthetic agents since S-ABA is toxicologically harmless and can also be used without reservations in ecological farming and for producing "biological" fruits.

For the purposes of the present invention, S-ABA, i.e. (S)-5-(1-hydroxy-2,6,6-trimethyl-4-oxo-2-cyclohexenyl)-3-methyl-cis/trans-2,4-pentanedienoic acid, is used exclusively. This substance is produced by fermentation and is commercially available.

S-ABA is to be distinguished from the abscisic acid-containing preparation designated as "Domain", which is an isomer mixture having a relatively low bioactivity, as compared to S-ABA, since it contains a high proportion of non-active isomers. S-ABA is the active isomer; in accordance with the present invention, only S-ABA is used instead of a mixture of isomers.

In accordance with the present invention, S-ABA is used preferably in fruit cultivation, particularly in pome fruit (e.g. apples, pears, quince, sorb [*Sorbus domestica*]), stone fruit (e.g. cherry, sour cherry, plum, Italian plum, peach, apricot, nectarine) and berry fruit (e.g. strawberries, currants, gooseberries, raspberries, blackberries). For the same, above-mentioned purposes, S-ABA can also be used advantageously in the cultivation of citrus fruits (e.g. oranges, clementines, mandarins, satsumas, grapefruit, pomelos, lemons, limes). The invention further encompasses the use of S-ABA in the cultivation of grain, particularly rice, lawn grass, or of oilseed crops, particularly rape, or of cotton, where an S-ABA-induced growth inhibition was observed too.

In the cultivation of pome fruit, S-ABA is used with particular preference in apple and pear cultures; in the cultivation of stone fruit, S-ABA is used with particular preference in cherry cultures.

In pome fruit cultivation, above all in apple and pear crops, the use according to the invention of S-ABA effects an improvement in fruit set and in the formation of parthenocarpic fruits. In these fruit crops, one can also observe an S-ABA-induced inhibition of vegetative growth.

The improvement of fruit set—which results in a correspondingly increased number of fruits per tree—is at least 5%, preferably at least 10%, especially preferably 15%, compared to untreated trees. These additionally produced fruits are almost exclusively parthenocarpic fruits. The increase in the number of fruits per tree is accompanied by a decrease in the average size of the fruits; however, in most cases (depending on the respective varieties) this is to be regarded as an advantage.

The S-ABA-induced growth inhibition can be determined from the average number of closed buds that are present on the trees. Treatment with S-ABA causes an almost complete closure of all buds, as compared to untreated trees. By application of S-ABA, the closure of the buds is initiated prematurely.

In stone fruit, particularly in cherry crops, the use according to the invention of S-ABA likewise produces an improvement in fruit setting. In these fruit cultures, an S-ABA-induced inhibition of vegetative growth can be observed in addition.

The S-ABA-induced improvement of the fruit set in stone fruit, especially in cherry crops, is preferably at least 50%, especially preferably at least 100%, and more preferably at least 125%, relative to the fruit set in untreated trees; this means that, on average, at least a doubling of the fruit set can be achieved.

According to the present invention, S-abscisic acid is preferably employed at a dosage of application of 0.2 to 20 g/h, especially preferably 1 to 10 g/ha, more preferably 1.5 to 2.5 g/ha. The optimal dose is 2 g/ha.

According to a particularly preferred embodiment, S-ABA is used in the form of a formulation which additionally contains at least one substance from the group of the UV-filters in order to prevent premature inactivation of the active substance by sunlight. Suitable UV-filter substances are known to those skilled in the art.

The active substance S-ABA can be formulated and applied in a manner known to those skilled in the art. Suitable types of formulations are, in particular, the following: water-dispersible powder (WP), water-soluble powder (SP), water-soluble concentrates (SL), emulsion concentrates (EC), concentrated emulsions (EW) such as oil-in-water and water-in-oil emulsions; sprayable solutions and emulsions, capsule suspensions (CS), dispersions on the basis of oil or water (SC), suspoemulsions, suspension concentrates, granules (GR) in the form of microgranules, spray granules, coated granules and adsorption granules, water-soluble granules (SG), water-dispersible granules (WG), microcapsules and tablets.

For applying S-ABA to the plant crops, it is possible to prepare, at the time of application, a tank mixture from an S-ABA-containing formulation, for example from one of the aforementioned formulations, by using water; this mixture can be sprayed onto the crops in a known manner, using a sprayer.

These individual formulation types are known in principle and are described, for example, in: Winnacker-Küchler, "Chemische Technologie" Volume 7, C. Hanser Verlag München, 4th Edition 1986; Wade van Valkenburg, "Pesticide Formulations", Marcel Dekker N.Y., 1973; K. Martens, "Spray Drying Handbook", 3rd Edition 1979, G. Goodwin Ltd. London.

The necessary formulation auxiliaries, such as inert materials, carrier materials, surface-active agents, solvents and further additives, are likewise known and are described, for example, in: Watkins, "Handbook of Insecticide Dust Diluents and Carriers", 2nd Edition, Darland Books, Caldwell N.J.; H. v. Olphen "Instruction to Clay Colloid Chemistry", 2nd Edition, J. Wiley & Sons, N.Y., Marsden "Solvents Guide", 2nd Edition, Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss. Verlagsgesell., Stuttgart 1976; Winnacker-Küchler "Chemische Technologie", Volume 7, C. Hanser Verlag München, 4. Edition 1986.

Wettable powders are preparations which can be evenly dispersed in water and which in addition to the active substance and apart from a diluent or inert substance also contain wetting agents, e.g. polyoxyethylated alkyl phenols, polyoxyethylated fatty alcohols and fatty amines, fatty alcohol polyglycol ether sulfates, alkane sulfonates or alkylaryl sulfonates and dispersing agents, e.g. sodium lignin sulfonate, sodium salt of 2,2-dinaphthylmethane-6,6'-disulfonic acid, sodium salt of dibutylnaphthalenesulfonic acid, or sodium salt of oleylmethyltauric acid.

Ethoxylated sorbitan esters and siloxanes have proved to be particularly suitable for the application of S-ABA. By adding these substances directly to the preparation or as a tank mixing partner, the amount of S-ABA can be reduced and its effects can be increased. Emulsifiable concentrates are produced by dissolving the active agent in an organic solvent, e.g. butanol, cyclohexanone, dimethyl formamide, xylene, or higher-boiling aromatics or hydrocarbons with addition of one or more emulsifiers. Substances that can be used as emulsifiers are, for example: alkylaryl sulfonic acid calcium salts, such as Ca-dodecyl benzene sulfonate, or non-ionic emulsifiers, such as fatty acid polyglycol esters, alkylaryl polyglycol ethers, fatty alcohol polyglycol ethers, propylene oxide-ethylene oxide condensation products (e.g. block polymers), alkyl polyethers, sorbitan fatty acid esters, polyoxyethylene sorbitan fatty acid esters or polyoxyethylene sorbite esters.

Granulates may be produced either by nozzle atomization of the active substance onto adsorptive, granulated inert material or by applying active substance concentrates by means of adhesives, e.g. polyvinyl alcohol, sodium salt of polyacrylic acid, or mineral oils to the surface of carrier substances, such as sand, kaolinites or of granulated inert materials. Suitable active agents can also be granulated in the manner usual for the production of fertilizer granulates—if desired, in mixture with fertilizers.

Apart therefrom the above-mentioned active agent formulations optionally contain the usual adhesive, wetting, dispersing, emulsifying or penetrating substances, solvents, filling agents or carrier substances.

In the case of liquid formulations, the content of S-ABA is preferably 1 to 250 g/l, especially preferably 2 to 100 g/l, more preferably 5 to 50 g/l. The portion of UV-filter(s) is preferably 0.05 to 10 g/l, especially preferably 0.1 to 5 g/l.

In the case of solid formulations (e.g. powders, granules, tablets), the content of S-ABA is preferably 1 to 50%-wt., especially preferably 2 to 25%-wt., more preferably 5 to 10%-wt. The portion of the UV-filter(s) is preferably 0.1 to 10%-wt., especially preferably 0.5 to 5%-wt.

For applying the formulations, which are present in commercial form, they are, if required, diluted in the usual manner, for example by means of water as liquid carrier in the case of wettable powders, emulsifiable concentrates, dispersions and water-dispersible granulates. Usually, S-ABA is sprayed onto the crops in a spray volume of 250 to 1000 l/ha.

S-ABA is preferably applied at the beginning of the vegetative period, particularly within the period from 1 to 3 weeks after flowering. This can either be a single application, or the application of S-ABA can be repeated once or several times during the vegetative period up to harvesting, preferably in intervals of 1 to 4 weeks, especially preferably in intervals of 2 to 3 weeks. In principle, it is possible to treat the plants with S-ABA during the entire vegetative period. For pome fruit and stone fruit, especially apple crops and cherry crops, the optimal treatment time is within the period immediately after flowering and up to 8 weeks after flowering.

According to a further embodiment of the invention, the first or only application of S-ABA takes place during flowering.

The invention further encompasses methods for promoting the fruit set and/or the production of parthenocarpic fruits in useful plants, especially in pome fruit or stone fruit, as well methods for inhibiting the growth in useful plants, each of said methods providing for a treatment of the plants with S-ABA. For further details, reference is made to the particulars given hereinabove.

According to a preferred embodiment of the method according to the present invention, pome fruit crops, especially apple or pear crops, are treated with S-ABA at a dosage of application of 0.2 to 20 g/ha, preferably 1 to 10 g/ha, especially preferably 1.5 to 2.5 g/ha, in order to improve fruit setting or/and to produce parthenocarpic fruits. The first or only treatment preferably takes place after flowering, especially preferably within a period of 1 to 3 weeks after flowering.

After that treatment, one, two or several further treatments can be applied, this/these further treatment(s) preferably being carried out 1 to 4 weeks, especially 2 to 3 weeks, after the first or the respective preceding treatment.

According to a further preferred embodiment of the method according to the invention, stone fruit cultures, especially cherry trees, are treated with S-ABA using an application dosage of 0.2 to 20 g/ha, preferably 1 to 10 g/ha, especially preferably 1.5 to 2.5 g/ha, in order to improve fruit setting. The treatment is preferably carried out immediately after the end of flowering or within a period of up to three weeks after flowering. After this treatment, at least one further treatment may be applied within the period up to harvesting, such further treatment(s) preferably taking place 1 to 4 weeks, especially 2 to 3 weeks after the first or after the respective prior treatment.

According to a further preferred embodiment of the inventive method, fruit crops, especially pome fruit or stone fruit crops, are treated with S-ABA using a dosage of application of 0.2 to 20 g/ha, preferably 1 to 10 g/ha, especially preferably 1.5 to 2.5 g/ha, to inhibit growth, said treatment being carried out during flowering or within a period of up to three weeks after flowering. After this treatment, at least one further treatment may be applied within the period up to harvesting, such further treatment(s) preferably taking place 1 to 4 weeks, especially 2 to 3 weeks after the first or after the respective preceding treatment. Particularly in fruit cultures showing excessive vegetative growth, repeated treatment with S-ABA is advantageous. Furthermore, the treatment of useful plants with S-ABA for the purpose of inhibiting vegetative growth is of advantage particularly in those cases where plants (e.g. grain, rape) could be weakened as a result of excessive longitudinal growth and therefore not possess sufficient stability to resist atmospheric influences, such as wind, rain, hail, etc.

The hereinbefore described methods are applicable in a corresponding manner in order to achieve the same effects in other fruit cultures, especially in citrus fruit or berry fruit.

The invention and the advantageous effects achieved thereby will be explained by means of the following examples.

Example 1

Promoting Fruit Set in Pome Fruit

Experimental period: 2003

Pome fruit crops treated: apple trees, variety Jonagored.

The fruit orchard was sprayed on 9 May, that is, three weeks after full flower (18 April). S-ABA was applied in a dose of 2 g/ha. For the control experiment, the same formulation, but without S-ABA, was used. The number of fruit trees per plot was 10.

The following results were obtained:

| Treatment: | Control | S-ABA |
|---|---|---|
| Yield [kg/tree] | 30.92 | 33.37 |
| Number of apples/tree | 110 | 129 |
| Apples in grade 75-85 mm [kg] | 8.43 | 15.54 |
| Apples in grade A2++ (75-85 mm) [kg] | 4.79 | 9.62 |

This experiment proves that S-ABA effects an improvement of fruit set. The number of apples per tree was increased by 17% as compared to the control; the yield (in kg) increased by 8%. Especially in the high grades, a distinct increase in yield (84%) was observed. This is also true of grade A2++, with optimal fruit color; the increase achieved here constituted a near doubling of the yield.

Example 2

Promoting Fruit Set, Production of Parthenocarpic Fruits and Inhibition of Growth in Pome Fruit Experimental period: 2004

Pome fruit crops treated: apple trees, variety Boskoop

The fruit orchard was sprayed on 23 April, that is, during full flower. A further plot was spayed on 20 May 2004. S-ABA was applied in a dose of 2 g/ha. For the control experiment, the same formulation, but with-out S-ABA, was used. The number of fruit trees per plot was 40.

The evaluation on 6 Jul. 2004 provided the following results:

| Treatment: | Control | S-ABA (23 April) | S-ABA (20 May) |
|---|---|---|---|
| Number of apples/tree | 34.6 | 35.4 | 42 |
| Number of unclosed buds/tree (crown tip excluded) | 6.6 | 1.66 | 0 |

These results prove that S-ABA causes an inhibition of vegetative growth. In the plots treated with S-ABA almost all buds were closed, independently of the time of treatment. The fruit set was not adversely affected by the treatment that took place during flowering. Application of S-ABA during flowering caused an inhibition of growth, without affecting the fruit set.

The buds or shoots in the crown tip of the trees were not taken into account because increased shoot growth frequently occurs in these places due to intensive cutting measures. In general, the growth of shoots in the crown tip is stronger than in the other regions of the tree crown.

As in Example 1, these results also prove that S-ABA promotes fruit set. However, this effect was observed only in the plot that had been treated with S-ABA three weeks after flowering (20 May). The total number of apples per tree could be increased by approximately 21%, as compared with the control.

Furthermore, it was found that in those trees treated with S-ABA parthenocarpic, pipless fruits were formed. The relative numerical portion of those fruits almost equals the number of the additionally formed fruits.

Example 3

Improvement of Fruit Set in Stone Fruit

Experimental period: 2004
Stone fruit crops treated: cherry trees, variety Summit
The fruit orchard was sprayed with S-ABA one week after flowering; the dose was 2 g/ha. For the control experiment, the same formulation, but without S-ABA, was used. The number of fruit trees per plot was 5.
The following results were achieved:

| Treatment: | Control | S-ABA |
|---|---|---|
| Yield [kg/tree] | 11.5 | 25 |

The results of the experiment prove that S-ABA brings about an improvement in fruit set. In the plot treated with S-ABA, the increase observed constituted a near doubling of the number of fruits, compared to the control plot (the size and weight of the individual fruits was almost the same in both plots); the weight per cherry was not significantly influenced by the treatment with S-ABA.

Parthenocarpic fruits were not observed in this case; parthenocarpy does not occur in stone fruits.

It was thus shown that the present application enables an increase in crop yield by improving the fruit set, without thereby adversely affecting the weight or quality of the individual fruits. On the contrary, the use of S-ABA additionally causes an improvement of fruit quality.

It was thus shown that the present application enables an increase in crop yield by improving the fruit set, without thereby adversely affecting the weight or quality of the individual fruits. On the contrary, the use of S-ABA additionally causes an improvement of fruit quality.

It was furthermore shown that in accordance with the present invention it is possible to achieve an inhibition of vegetative growth by application of S-ABA.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for promoting fruit set and/or for producing parthenocarpic fruits in fruit cultivation, comprising treating fruit plants with S-abscisic acid during a period of 1 to 3 weeks after flowering thereby promoting fruit set and/or producing parthenocarpic fruits in the fruit plants.

2. The method according to claim 1, wherein the plants are selected from the group consisting of apple, pear, cherry and citrus trees, and berry fruit crops.

3. The method according to claim 1, wherein the S-abscisic acid is used in a dosage of application of 0.2 to 20 g/ha.

4. The method according to claim 1, wherein the S-abscisic acid is used in combination with at least one further substance from the group of the UV-filters.

5. The method according to claim 1, wherein up to harvesting, the treatment is repeated at least once.

6. The method according to claim 1, wherein the fruit plants are pome fruit crops or stone fruit crops.

7. The method according to claim 3, wherein the dosage of application is 1 to 10 g/ha.

8. The method according to claim 7, wherein the dosage of application is 1.5 to 2.5 g/ha.

9. The method according to claim 5, wherein the treatment is repeated at intervals of 1 to 4 weeks.

10. The method according to claim 9, wherein the treatment is repeated at intervals of 2 to 3 weeks.

* * * * *